United States Patent [19]

Radhakrishnan

[11] Patent Number: 5,516,355
[45] Date of Patent: May 14, 1996

[54] METHOD OF PREPARATION OF COMPOSITIONS FOR AN AMALGAM

[76] Inventor: Subramaniam Radhakrishnan, 123 Jalan Terasek Lapan (8), Bangsar Baru, Kuala Lumpar 59100, Malaysia

[21] Appl. No.: 240,784

[22] PCT Filed: Nov. 13, 1992

[86] PCT No.: PCT/GB92/02101

§ 371 Date: Nov. 21, 1994

§ 102(e) Date: Nov. 21, 1994

[87] PCT Pub. No.: WO92/16860

PCT Pub. Date: Oct. 1, 1992

[30] Foreign Application Priority Data

Nov. 13, 1991 [MY] Malaysia ............... PI 9102099

[51] Int. Cl.$^6$ ............... C22C 5/08; A61C 5/00
[52] U.S. Cl. ............... 75/351; 75/741; 75/744; 433/207
[58] Field of Search ............... 75/351, 388, 390, 75/391, 741, 742, 744, 255; 423/27, 28, 34, 98, 109; 216/108; 433/207

[56] References Cited

U.S. PATENT DOCUMENTS 5,242,305  9/1993  O'Brien ............... 420/503

5,413,617  5/1995  Lin et al. ............... 75/741

FOREIGN PATENT DOCUMENTS

| 124213 | 11/1984 | European Pat. Off. ............... 75/741 |
| 158626 | 10/1985 | European Pat. Off. ............... 75/744 |
| 2338696 | 8/1977 | France . |
| 432881 | 7/1935 | United Kingdom ............... 75/741 |
| 641300 | 8/1950 | United Kingdom . |
| 2188649 | 10/1987 | United Kingdom . |
| 87001732 | 3/1987 | WIPO ............... 75/744 |

OTHER PUBLICATIONS

Patent Abstracts of Japan V.5, No. 144 (C–71)(816) Sep. 11, 1981 of 56–077, 213.

*Primary Examiner*—David A. Simmons
*Assistant Examiner*—Margery S. Phipps
*Attorney, Agent, or Firm*—Westman, Champlin & Kelly

[57] ABSTRACT

The invention relates to a method of preparing a dental amalgam that is devoid of harmful free mercury, to be used as a filler for dental cavities. In particular the invention relates to processes by which two separate compositions characterized as treated silver and silver-mercury compound are formed, which are then used in a mixture with mercury to form the dental amalgam.

8 Claims, No Drawings

METHOD OF PREPARATION OF COMPOSITIONS FOR AN AMALGAM

This invention relates to a method of preparing a dental amalgam that is devoid of harmful free mercury, to be used as a filler for dental cavities and in particular the invention relates to processes by which two separate compositions characterised as treated silver and silver-mercury compound are formed which are then used in a mixture with mercury to form the dental amalgam.

BACKGROUND OF THE INVENTION

Compositions for filling dental cavities presently available usually comprises of dental alloys mixed with mercury. The dental alloys include at least three metals. A typical alloy would include Silver, Tin and Copper. Small percentages of one or more additional metals like Zinc, Indium, Palladium and the like metals may be added. These dental alloys are available either in fine powder or as tablets (i.e. compressed powder). The dental alloy is mixed with mercury to form a putty or plastic mass known as amalgam which is packed into a tooth cavity as a filling. Among the three metals, namely Silver, Tin and Copper, Silver is the only metal used in dental alloys that can completely react with mercury to form a silver-mercury compound or silver amalgam.

Recently research scientists have established that there is "free" mercury i.e. unreacted mercury present within the amalgam fillings in the mouth. The free mercury can vapourise in the mouth from the fillings due to the higher temperatures experienced in the mouth. The mercury vapour can be inhaled into the lungs, where it is absorbed into the bloodstream. Studies have shown deposits of mercury in brain and kidney tissues that have originated from such fillings. Mercury also causes bleeding gums and skin reactions.

This "free" mercury has contributed to various medical problems as well as in certain patients, hypersensitivity reactions. In fact, in recent times, dental experts in Sweden have recommended to the authorities to ban the use of such "amalgams" in pregnant women to prevent genetic damage to the fetus as there is evidence to show that "free" mercury from the mother can via the transplacental route, affect the fetus.

A lesser problem in the use of conventional dental alloy amalgams is the chemical corrosion caused in the oral cavity. As tin and copper are prone to corrosion, the corrosion process continues in the mouth throughout the relatively short span of the life of the fillings.

In another aspect of the history of amalgam in dental fillings, silver fillings were mixed with mercury to form a putty which was filled into the tooth cavity. Unfortunately the mixed amalgam due to expansion property upon setting caused severe pain to the patient and protruded from the surface of the cavity and in bad cases even fractured the crowns of the teeth. In either case, the patient suffers severe pain, resulting in the extraction of the tooth. For this reason, silver in the original is not used alone with mercury to form the amalgam.

Tin is added to silver to make an alloy of silver and tin which alloy is then mixed with mercury to form the amalgam. Tin causes contraction on setting. This contraction can be offset by the expansion property in the purely silver-mercury amalgam. But the main disadvantage is that the mercury in the resultant amalgam contains unreacted mercury (in the free state) within the fillings.

To increase the strength of the amalgam filling varying percentage of copper was added to silver-tin alloy. Unfortunately the resultant amalgam still has mercury in the free state. As stated before, mercury vapour formation within the mouth can cause ill-effects to the patient.

Simply stated, for more that 150 years the search for a dental amalgam that is devoid of the toxic and harmful effect of free mercury has eluded researches.

SUMMARY OF THE INVENTION

Thus it is an object of the present invention to provide an amalgam for dental filling that substantially eliminates the problems elaborated above, in particular to provide an amalgam which is devoid of free mercury.

According to this invention, there is provided a method for the production of an amalgam for filling a dental cavity, which when used as an amalgam filling, is devoid of free mercury. The production of the compositions comprises of a process for preparing treated silver in a fine powder form and a process for the production of silver-mercury compound; the amalgam is produced by mixing the above two compositions with a recommended quantity of mercury, to produce the amalgam.

To obtain all the benefits of the invention it is desirable to use all the novel steps hereinafter described. Accordingly, the process of the invention comprises one or more of the following steps:

(a) using as starting materials, metallic silver and tin of high purity to form a homogeneous alloy of silver and tin and then reducing the resultant alloy to a fine powder;

(b) reacting the fine powder from (a) with hydrochloric acid to remove the tin and then siphoning off the Tin solution leaving behind undissolved solid particles and thereafter repeating the above reaction with fresh amount of hydrochloric acid until all the tin is removed and the appearance of the remaining solid particles changes from the original dark greyish colour to a yellowish-brown colour, which forms the composition referred to as the treated silver.

(c) reacting advantageously metallic granules silver metal of high purity and mercury with nitric acid and thereafter precipitating silver-mercury from the resultant Nitrate solution of silver and mercury by adding copper of high purity then removing any traces of acid from the precipitate by filtering and washing the precipitate repeatedly with preferably warm water and drying the acid-free precipitate which forms the composition referred to as the silver-mercury compound.

(d) mixing the treated silver from (b) with the silver-mercury precipitate from (c).

(e) then mixing the composition from (d) with a recommend quantity of mercury to produce the final amalgam to be used for filling a tooth cavity.

By optimizing the various steps described above dental amalgam that is devoid of harmful free mercury is obtained.

DESCRIPTION OF THE PREFERRED EMBODIMENTS

Preferred conditions for optimization through repeated experiments are described hereinafter.

(a) By repeated experiments, Silver and Tin of high purity in the range of ratios between 60%:40% to 80%:20% by weight respectively were tried to form the alloy mass. The best results were obtained when silver and tin were mixed in the ratio of 72%:28% by weight respectively to form the alloy mass. This alloy was obtained by melting the above mixture in a furnace. Silver and tin in the range of ratio between 60%:40% to 80%:20% other than the said best ratio by weight respectively are although workable they did not give the best result. The homogeneous alloy mass was then lathed or ground to obtain a coarse powder which powder was then ball milled to a fine powder.

(b) The fine powder from (a) was reacted with hydrochloric acid at elevated temperatures, i.e. the fine powder of the alloy was mixed with hydrochloric acid and heated to boiling point temperatures to remove the dissolved Tin. The above treatment with the acid was repeated several times on the remaining solid particles after siphoning off the treated acid solution, so as to remove the dissolved Tin. The process of acid treatment was stopped when the original dark grey colour of the solid particles changed to a yellowish brown colour. The remaining solid particles formed the composition referred to as treated silver which filtered and washed several times until it was acid free and was then dried and stored.

(c) By repeated experiments metallic silver granules of high purity and mercury were weighed in a range of ratio between 1:1 to 1:2.2 by weight respectively to determine the optimum ratio to obtain best results; a ratio of 1:1.9 by weight respectively gave the best results for obtaining the silver-mercury compound. The metals as selected in the ratios above were dissolved together in nitric acid and the common solution of silver-mercury Nitrate was then preferably diluted by the addition of water. Alternatively the metals in the desired ratios were reacted with nitric acid separately and thereafter the solutions were mixed together. The silver-mercury compound was precipitated by an "exchange process" by the introduction of copper metal of high purity into the solution. The precipitated powder was filtered then washed with warm water until acid free. The powder so obtained being the composition referred to as the silver-mercury compound.

(d) By repeated experiments the treated silver from (b) was mixed with silver-mercury compound of (c) in the range of ratio between 50:50% to 80:20% by weight respectively and the best results of the mixture were obtained in the ratio of 55% to 45% by weight respectively.

(e) Again by repeated experiments, the resultant mixture from (d) was mixed with a mercury at ambient temperature to form an amalgam, the range of ratio of mixture to Mercury by weight respectively were tried between 1:1.18 to 1:1.4 although the final amalgam was formed to be workable but by far the best results were obtained when mixed in the ratio of 1:1.18 by weight respectively.

A preferred embodiment of the processes of production of the compositions and amalgam to get the best results according to the invention is described below.

The method of preparation of the treated silver composition is described below. To form a silver and tin alloy, Silver and Tin of high purity is weighed in the ratio of 72%:28% by weight respectively. The metals are melted together in a furnace to form an alloy mass, preferably in the form of a cylindrical bar. The alloy bar is then reduced to fine powder by means known to the art. In the present invention the alloy bar is lathed to obtain a coarse powder, which powder is subsequently ball milled to fine powder. This fine powder is treated with hydrochloric acid and heated to boiling point, then siphoned and the process of acid treatment is repeated until the original dark grey colour of the solid particles turns into yellowish brown colour when all the tin present in the alloy is removed by this chemical process.

The remaining solid particles in the acid solution is treated silver. The treated silver solid particles as powder is filtered, then washed repeatedly with warm water to remove all traces of acid from the powder it is then dried. This treated silver in fine powder form may be referred to as composition "A".

In a separate process, advantageously metallic silver granules and mercury of high purity are used in the ratio of 1:1.9 by weight respectively for best results. The silver and mercury selected in the ratio above is reacted with nitric acid either separately or together whereby both the silver and mercury go into solution. The solution of silver and mercury, if dissolved in the nitric acid separately the solutions are later mixed together. The resultant solution is diluted by adding water. Silver-mercury compound is then precipitated by the introduction of copper metal into the solution. The precipitated powder is removed by filteration from the solution and washed with warm water until it is acid free. Thereafter it is dried. The resultant silver-mercury compound may be referred to as composition "B".

As the next step, composition A and composition B are mixed together preferably in the ratio of 55% of A to 45% of B by weight for best results. This resultant mixture is called mixture "C".

Mixture "C" is mixed with mercury at ambient temperature in the ratio of mixture "C" to Mercury at 1:1.18 by weight for obtaining the best working properties of the amalgam (D).

The resultant amalgam D is used to fill dental cavities in the conventional manner.

An important feature of the invention is that the filling composition is devoid of free mercury.

Those skilled in the art will appreciate that the invention described is herein susceptible to variations and modifications other than those specifically described. It is to be understood that the invention includes all such variations and modifications. The invention also includes all of the steps, features, compositions and compounds referred to or indicated in this specifications, individually or collectively, and any of all combinations of any two or more of the steps of or features.

I claim:

1. A process for making dental amalgam for use as a dental filler characterized by the preparation of a mixture comprising a treated silver composition and a silver-mercury compound, comprising:

preparing the treated silver composition from metallic silver and tin of high purity by the steps of forming a homogeneous alloy of silver and tin, reducing the alloy to form a fine powder, reacting said powder with hydrochloric acid to remove the dissolved tin from the alloy thereby leaving solid particles of treated silver in the acid solution, the process of hydrochloric acid treatment being carried out several times on the solid particles until there is a noticeable color change in the solid particles from a dark grey to a yellowish brown color, filtering the yellowish brown solid particles and washing them several times with warm water to remove all traces of the acid, and drying the particles to form the treated silver composition;

preparing said silver mercury compound from granules of metallic silver of high purity and mercury by the steps of reacting either a mixture of the granules and the mercury with nitric acid to form a nitrate solution, or reacting the silver granules and mercury separately with nitric acid each to form separate solutions, which two solutions are subsequently mixed to form a combined nitrate solution, diluting the nitrate solution by adding water, and introducing metallic copper of high purity which results in a precipitate of a silver mercury composition, which is filtered and washed several times with warm water to remove traces of acid and is then dried to result in the silver-mercury compound, and combining said mixture with mercury to form a dental amalgam that is devoid of harmful free mercury.

2. A process as claimed in claim 1, characterized in that the silver and tin are mixed in the range of percentage ratios between 60%:40% and 80%:20% by weight respectively to form the silver and tin alloy.

3. A process as claimed in claim 2 characterized in that the silver and tin are mixed in the ratio of 72%:28% by weight respectively.

4. A process as claimed in claim 3 characterized in that the weights of silver and mercury are in the ratio of 1:1.9 by weight before they are reacted with the nitric acid.

5. A process as claimed in claim 1 characterized in that the composition of treated silver and the composition of silver-mercury are mixed in the range of percentage ratios between 80%:20% to 50%:50% by weight.

6. A process as claimed in claim 5, characterized in that the treated silver composition and the silver-mercury composition are mixed in the percentage ratio of 55%:45% by weight.

7. A process as claimed in claim 1 characterized in that the mixture of treated silver and silver-mercury compositions is mixed with mercury in the range of ratios between 1:1.18 to 1:1.4 by weight, to form the dental amalgam.

8. A process as claimed in claim 7, characterized in that the mixture of the treated silver composition and silver-mercury composition is mixed with mercury in the ratio of 1:1.18 by weight respectively, to form the dental amalgam.

\* \* \* \* \*